(12) United States Patent
Dam et al.

(10) Patent No.: US 7,694,570 B1
(45) Date of Patent: Apr. 13, 2010

(54) NON-INVASIVE DRY COUPLED DISPOSABLE/REUSABLE ULTRASONIC SENSOR

(75) Inventors: Naim Dam, Muttontown, NY (US); Andre Granin, Wantagh, NY (US); Glen Melder, Lake Ronkonkoma, NY (US)

(73) Assignee: Cosense, Inc, Hauppauge, NY (US)

( * ) Notice: Subject to any disclaimer, the term of this patent is extended or adjusted under 35 U.S.C. 154(b) by 378 days.

(21) Appl. No.: 11/731,212

(22) Filed: Mar. 30, 2007

(51) Int. Cl.
*G01N 29/00* (2006.01)
*H01L 41/00* (2006.01)

(52) U.S. Cl. .............................. 73/644; 73/649; 73/721; 310/328

(58) Field of Classification Search .................... 73/644, 73/645, 649, 776, 778, 721, 861.27, 861.28
See application file for complete search history.

(56) References Cited

U.S. PATENT DOCUMENTS

| | | | |
|---|---|---|---|
| 4,864,724 A | 9/1989 | Bergstrom | 29/854 |
| 4,904,894 A * | 2/1990 | Henry et al. | 310/328 |
| 5,408,882 A * | 4/1995 | McKinley et al. | 73/597 |
| 5,644,093 A | 7/1997 | Wright et al. | 73/866.5 |
| 6,397,656 B1 | 6/2002 | Yamaguchi et al. | 71/1.82 |
| 6,781,287 B1 | 8/2004 | Dam | 310/334 |
| 6,969,943 B2 * | 11/2005 | Hashimoto et al. | 310/334 |
| 7,004,824 B1 * | 2/2006 | Madanshetty | 451/60 |

* cited by examiner

*Primary Examiner*—J M Saint Surin
(74) *Attorney, Agent, or Firm*—Gordon D. Coplein

(57) ABSTRACT

A non-invasive dry coupled disposable/reusable ultrasonic sensor has a housing and a piezoelectric element at one end of the housing to which connected signal leads are connected that extend out from the housing. A piece of double-sided adhesive tape has one adhesive side secured directly to the face at the one end of the housing with the other adhesive side to be secured directly to the outer surface of a pipe or vessel. The tape can cover the entire face of the one end of the housing or only that part that the piezoelectric element faces.

17 Claims, 3 Drawing Sheets

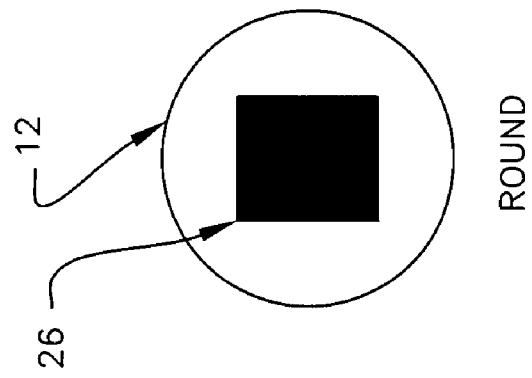
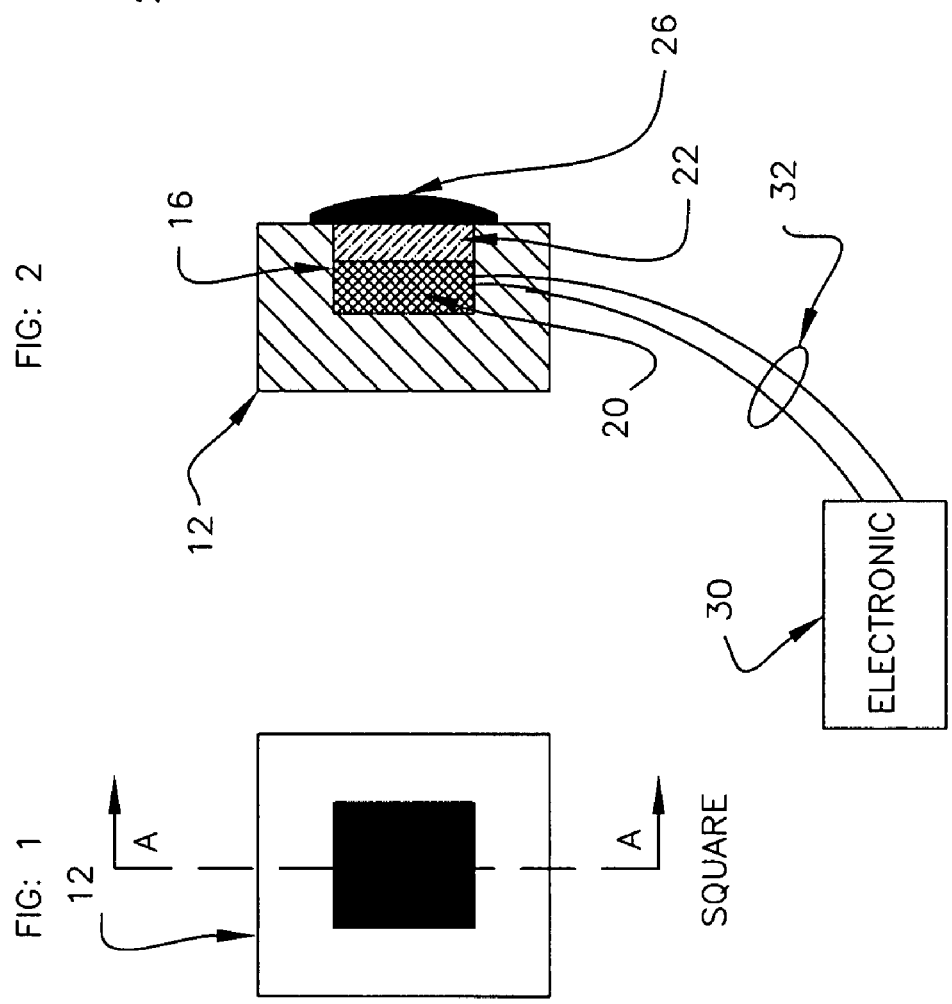
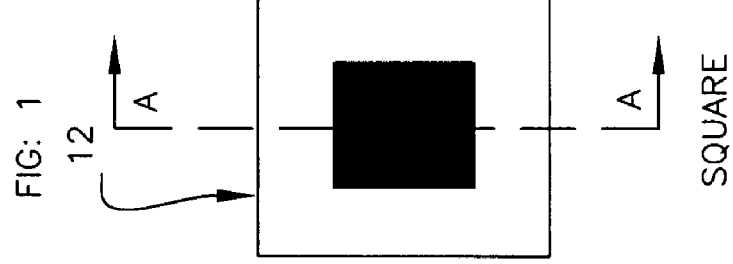

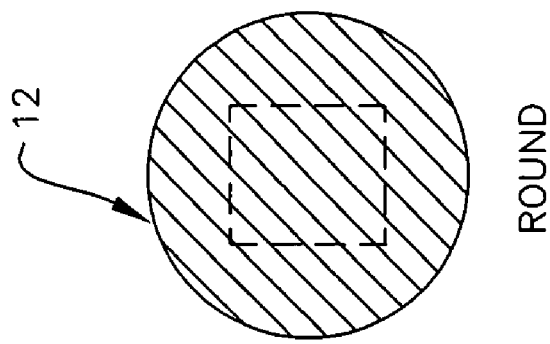
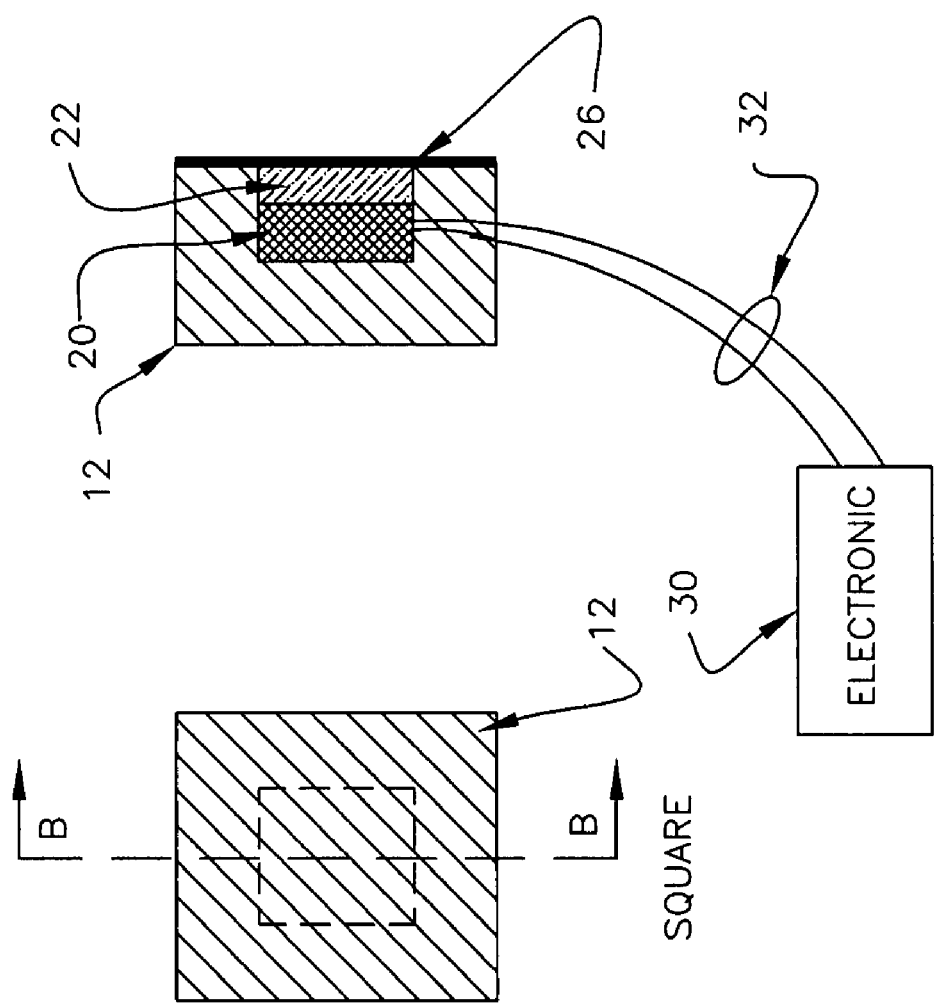
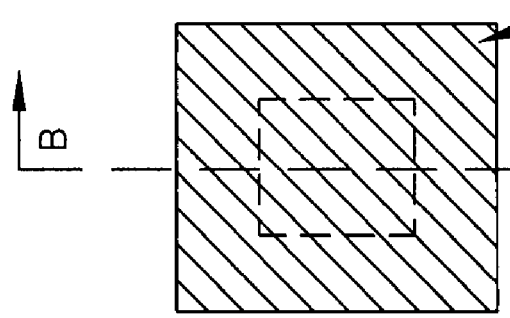

NON-INVASIVE DRY COUPLED DISPOSABLE/REUSABLE ULTRASONIC SENSOR

FIELD OF THE INVENTION

The invention relates to ultrasonic transducers, or sensors, of the type that do not have to contact the liquid to sense its presence and more particularly to one which can be adhesively mounted to the outer surface of a vessel or tube to sense the liquid therein without the need of a coupling compound between the transducer and the vessel or tube.

BACKGROUND OF THE INVENTION

Transducers, or sensors, for transmitting and receiving ultrasonic energy in applications involving liquids are well known. A typical application for such transducers is in liquid level sensing to sense the height of a liquid in a tube or pipe or a container or other vessel, such as a tank. The term vessel as used hereinafter includes any type of a vessel such as a tank or other liquid container and the term tube includes pipes of metal or plastic and tubing of flexible or rigid material. Another application is use with a tube to transmit and receive ultrasonic energy across a defined space so as to sense the presence of air bubble or particles flowing in the tube so that they can be counted and characterized, such as by size, by a computer. Still a further application is in flow meters where the rate of flow in a pipe is measured.

One widely used form of such transducer has a housing that contains a piezo-electric element. The housing is mounted to the vessel or tube with the front end of the housing extending trough a hole placed to be in direct contact with the liquid. The ultrasonic energy is coupled directly to the liquid to sense its presence or the energy dissipates in air when no liquid is present.

Another type of ultrasonic transducer is of the non-contact type, such as disclosed in U.S. Pat. No. 4,630,245, granted Dec. 16, 1986. Here, the transducer housing is of a rigid material, such as a plastic, and is fixedly mounted, such as by a clamp or strap, to the outside of the vessel or tube in which the liquid being sensed is present. The non-contact type transducer has an advantage in that no hole has to be made in the vessel or tube to which it is mounted but it requires a coupling compound, such as Vaseline, or silicon grease, between the housing and the vessel or tube. The coupling compound is needed so that there will be no air gaps between the end of the transducer housing through which ultrasonic energy enters or is transmitted and the vessel or tube since this would adversely affect the transmission and reception of the ultrasonic energy from the transducer to the wall of the vessel or tube and thereafter to the liquid or air therein.

Application of the coupling compound in the foregoing type of non-contact transducer is another step required in the mounting of the transducer. The need for using a coupling compound also limits the use of such a transducer, for example, in an application for sensing the liquid level in bottles moving rapidly past a fixed inspection point on an assembly line. Here, it would not be possible to apply the coupling compound to each of the bottles. Also, in some applications, the use of a coupling compound can adversely affect the appearance of the tube or vessel. Further, in sensitive sanitary applications such as drug and food processing, the use of such coupling compound should or must be avoided. Another disadvantage in this type of non-contact transducer is that it is fixed in position and cannot be easily moved.

U.S. Pat. No. 6,781,287 to Naim Dam, et al, granted Aug. 24, 2004, which is assigned to the assignee of the subject application discloses an ultrasonic transducer that has a capsule, or head, of a flexible and deformable material that contacts the outer surface of the pipe or vessel. The piezoelectric element is within the capsule which also contains a fluid, such as oil, that serves as the coupling agent. While this transducer does not require a coupling agent external of the transducer housing, it is somewhat complicated and relatively expensive to manufacture.

Accordingly, a need exists for a non-contact type ultrasonic transducer that is not subject to the limitations of requiring either an externally applied coupling compound or external mounting devices. It is also preferred that such a transducer be as economical as possible so that it can be disposable when used in certain applications, such as medical procedures.

BRIEF DESCRIPTION OF THE INVENTION

In accordance with the invention, a non-contacting type ultrasonic transducer is provided having a housing in which the piezo-electric element is mounted. One face of a piece of double-sided adhesive tape is fastened onto the front end of the housing which is to face the vessel or tube on which the transducer is to be mounted. The other face of the double-sided tape is to be mounted directly to the vessel or tube. In one embodiment of the invention, the entire front end of the transducer housing is covered by the adhesive tape and in another embodiment only the portion of the front end in which the piezoelectric element is mounted is covered by the adhesive tape. The double-sided adhesive tape is preferably one that has a rubber based adhesive which is sufficient to provide the coupling between the piezoelectric element in the transducer housing and the outer surface of the vessel or tube on which the transducer is mounted so that ultrasonic energy can be transmitted into the vessel or tube or received after passing through it.

BRIEF DESCRIPTION OF THE DRAWINGS

Other objects and advantages of the present invention will become more apparent upon reference to the following specification and annexed drawings in which:

FIG. 1 is a front view of one embodiment of the transducer of the invention;

FIG. 2 is a cross-sectional view of to transducer taken along line A-A of FIG. 1;

FIG. 3 is a front view of another type of transducer in accordance with the first embodiment;

FIG. 4 is rear view of a second embodiment of the transducer of the invention;

FIG. 5 is a cross-sectional view of the transducer of FIG. 4 taken along lines B-B of FIG. 4;

FIG. 6 is a rear view of another type of transducer in accordance with the second embodiment.

DETAILED DESCRIPTION OF THE INVENTION

Figure 7:
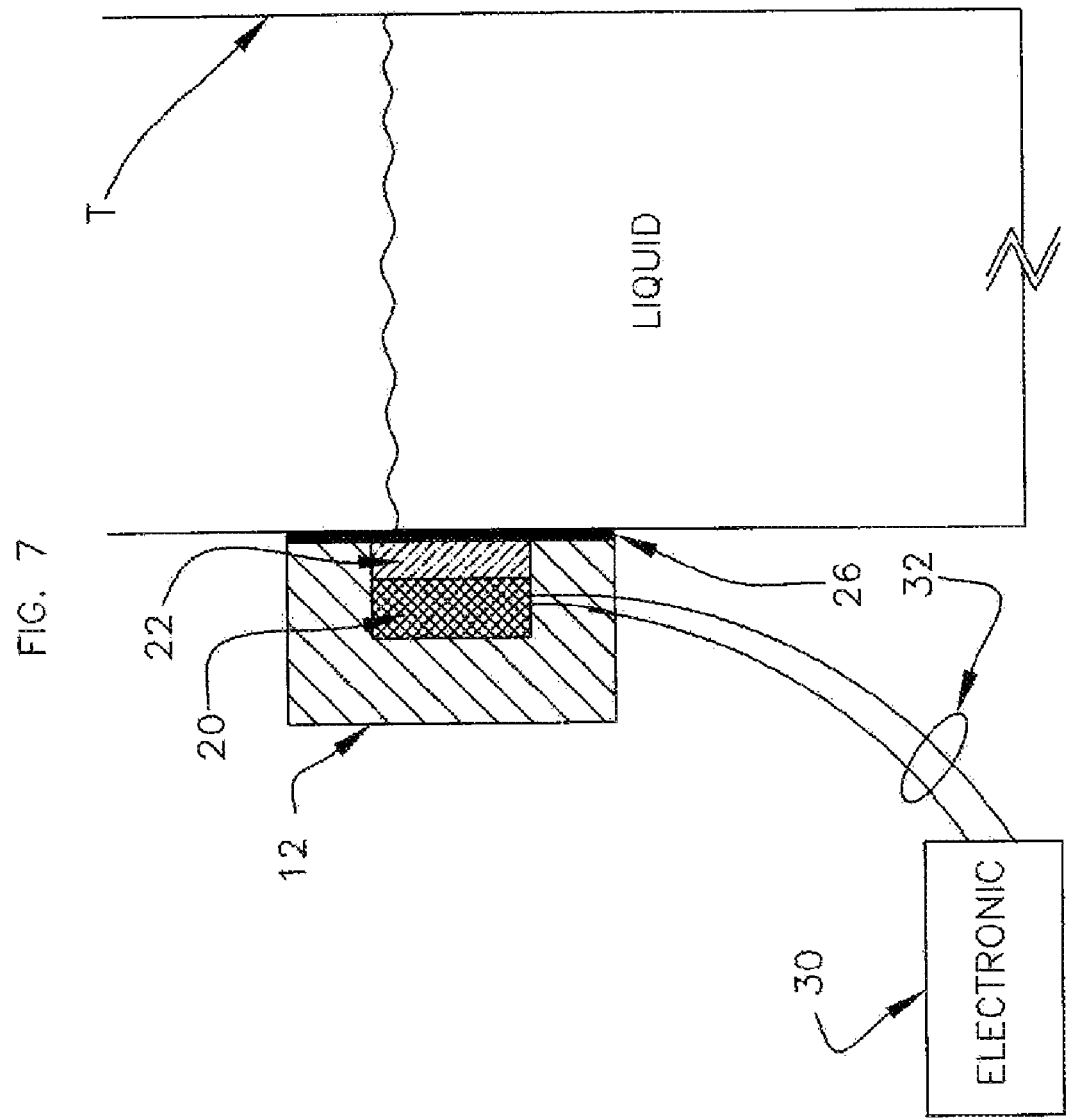
FIG. 7 is a view of transducer of the invention mounted to the wall of a vessel.

Referring to FIGS. 1-2, the transducer 10 is formed by an outer housing 12, which can be of metal or plastic. Plastic is preferred to reduce the weight. In FIGS. 1-2 the housing 12 is illustratively shown as generally square in shape and in FIG. 3 is shown as cylindrical. Any other shape can be used, such as rectangular or part cylindrical and part rectangular or any other suitable desired shape.

From the front of the housing there is a blind bore 16 that forms a pocket into the back of which a piezoelectric transducer element 20 is mounted. The bore 16 can be circular or the housing 12 can be cast with the bore being square or rectangular. The piezoelectric element 20 fits in the bore and can be held within it by an epoxy cement. The transducer element can be of PZT (Lead Zirconate Titanate) or PVDF (Polyvinylidene Fluoride), both being conventional in the art. Mounted In the front of the piezoelectric element 20 in the bore 16 and having a face that is flush with the outer face of the front end of the housing 12 is a matching element 22 can be of Teflon or other suitable material such as silicon rubber. This also can be held within the housing bore by an interference fit or an adhesive, such as an epoxy. All of this is conventional in the art.

The piezoelectric element 20 within the housing 12 has electrodes and is connected to an electronic unit 30 through leads 32. Electronic unit 30 can contain one or both of a transmitter that produces ultrasonic energy and supplies it over the leads 32 to the piezoelectric element or a receiver, usually including an amplifier, that amplifies the electrical signal produced by the piezoelectric element after receiving ultrasonic energy transmitted through the vessel or tube. All of this also is conventional in the art.

A piece of double-sided adhesive tape has one face 26 fixed on the outer face of the matching element 26 over and around part of the front face of the housing 12. The other, outer, face of the piece of adhesive tape 26 is to be placed on the vessel or tube to which the transducer is to be mounted. A suitable type of adhesive tape is one with a rubber adhesive, such as 3M P/N 9443 or 3M P/N 401 0. These tapes are about 1.0 to 2.0 mil thick and the adhesive is on a plastic web such as polypropylene. These types of tape have been found to be suitable to hold the transducer amounted to the vessel or tube and also to permit the transducer to operate without the need for a coupling agent between the front face of the matching element 22 and the vessel or pipe. In accordance with the knowledge of the art the tape thickness should be an odd number multiple of a quarter wavelength of the frequency of the ultrasonic energy. In a practical application, a protective piece of paper (not shown) is placed on the outer face of the adhesive tape 26.

Typical specifications for transducers of the invention are:

| | |
| --- | --- |
| Height | 0.5 inches to 1.5 inches |
| width | 0.5 inches to 1.5 inches |
| diameter | 0.5 inches to 1.5 inches |
| thickness | 0.15 inches to 0.40 inches |
| housing material | EBS or other plastic material |
| Piezoelectric element | PZT or PVDF |
| Matching element | Teflon or silicon rubber |
| Weight | less than 2 ounces |
| Tape | 3M types 9443, 4010 |

The dimensions of the piezoelectric element are selected depending upon the frequency of the application. Typical frequencies are from 500 Khz to 5 MHz FIG. 3 shows a modification of the transducer of FIGS. 1-2. Here, the housing 12 is round instead of square. The mounting of the piezoelectric element 20 and matching element 22 are the same as it is the fixation of the piece of the double-sided adhesive tape 26. The housing 12 can have a diameter from 0.5 inches to 1.5 inches. The other specifications for the transducer of FIG. 3 are the same as those given above.

FIGS. 4 and 5 show a second embodiment of the transducer is similar to that of the transducer FIGS. 1-2. Here, the difference is that the double-sided adhesive tape 26 completely covers the front face of the housing 12. This provides more surface area for the adhesive tape to adhere to both the housing and 12 and to the vessel or tube to which the transducer is to be affixed. In this embodiment of the invention, the typical specifications are the same as those given above.

FIG. 6 is a modification of the embodiment of the transducer of FIGS. 4-5 in which the housing 12 is round, as in FIG. 3. Here also, as in the case of FIG. 5, the piece of double-sided adhesive tape 26 covers the complete front face of the housing 12. The other specifications of this transducer are similar to those given above.

The process for making the transducer 10 follows. First, the piezo-electric element 20 is selected for the required operating frequency, which can illustratively be from 500 Khz-5 MHZ. Electrodes are plated on the element and the ends of the lead wires 32 are attached. The assembly of the piezoelectric element and the wires is inserted into the housing 12 and the impedance matching element 22 is also placed in the housing in contact with the piezoelectric element. A piece of the double-sided adhesive tape 26 is cut to the appropriate size, such as to cover the entire front end of the transducer housing or me that portion of the housing having the piezoelectric element.

In the use of the transducer 10, the protective covering is peeled off of the outer face of the double sided adhesive tape. As illustratively shown in FIG. 7 the outer face of the adhesive tape 26 is mounted directly onto the other outer surface of the wall of a vessel, a tank or bottle T, containing a liquid. It also can be mounted directly to the outside of any other type of vessel or tube. A coupling is effected through the adhesive tape 26 that permits the transmission and reception of ultrasonic energy between the piezoelectric element 20 and the vessel or tube wall. The transducer can be de-mounted simply by pulling the outer face of the double-sided adhesive tape away from the wall of the vessel or pipe. To facilitate removal, the tape can be provided with a tab that overhangs the housing periphery and can be easily grasped for pulling. After removal from the vessel or tube the transducer can be disposed of or re-used again. In the latter case, if the tack of the adhesive outer face is not sufficient for re-installation, then the original piece of tape 26 can be removed from the transducer and a new piece applied.

As seen, the transducer of the invention is simple to construct and simple to mount to the vessel or tube. It is non-invasive since it is mounted on the outside of the wall of the vessel or tube on which it is mounted, it is dry-coupled since it requires no coupling compound and it requires no external mounting device such as a strap. Therefore, it's mounting onto and removal from the vessel or tube is easy and quick.

The transducer 10 of the invention is used in conventional applications, such as measuring liquid level in a vessel from a vessel side wall, point level sensing, or from the bottom of the vessel in a "bottom up" continuous measurement application that determines the height of the liquid in the vessel. One or more of the transducers can be placed on the outer wall of a pipe to sense the flow rate of a liquid within the pipe. Since the transducer is relatively inexpensive to make it can be used for disposable applications, such as in the medical field.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

We claim:

1. An ultrasonic transducer for detecting liquid in a pipe or vessel comprising:
   a housing;
   a piezoelectric element within said housing facing one end of said housing and having connected signal leads that extend out from said housing to be connected to an electronic circuit that is to at least one of supply electrical energy to be transmitted by said piezoelectric element as ultrasonic energy and/or receive ultrasonic energy to be supplied to the electronic circuit as electrical signals;
   and a piece of double sided adhesive tape having one adhesive side secured directly to the outer face of said one end of said housing with the other adhesive side to be secured directly to the outer surface of the wall of a pipe or vessel and being of a material and thickness to effectively couple the ultrasonic energy in at least one of transmitting and receiving directions between said piezoelectric element, the pipe or vessel wall on which the transducer is mounted and a liquid in the pipe or vessel.

2. The ultrasonic transducer as claimed in claim 1 wherein said tape is continuous.

3. The ultrasonic transducer as claimed in claim 1 wherein said tape has a cutout portion that corresponds to the shape of an opposing face of said piezoelectric element.

4. The ultrasonic transducer as claimed in claim 1 wherein the adhesive of said tape is one of acrylic, silicone and rubber adhesive.

5. The ultrasonic transducer as claimed in claim 1 wherein the thickness of the tape is from 1.0 to 20.0 mil thick.

6. The ultrasonic transducer as claimed in claim 1 wherein said transducer housing face has length and width or a diameter of from 0.5 inches to 1.5 inches.

7. The ultrasonic transducer as claimed in claim 6 wherein said transducer has a weight of not greater than 2 ounces.

8. The ultrasonic transducer as claimed in claim 7 wherein said tape is of polypropylene material and the adhesive of said tape is one of acrylic, silicone and rubber adhesive.

9. The ultrasonic transducer as claimed in claim 8 wherein the thickness of the tape is from 1.0 to 20.0 mil thick.

10. The ultrasonic transducer as claimed in claim 8 wherein said piezoelectric element is to operate at a frequency in the range of 500 Khz to 5 MHZ.

11. The ultrasonic transducer as claimed in claim 10 wherein the thickness of the tape is from 1.0 to 20.0 mil thick.

12. The ultrasonic transducer as claimed in claim 8 wherein the thickness of the tape is from 1.0 to 20.0 mil thick.

13. The ultrasonic transducer as claimed in claim 12 wherein the adhesive of said tape is one of acrylic, silicone and rubber adhesive.

14. The ultrasonic transducer as claimed in claim 1 wherein said tape covers substantially the entirety of said outer face of said one end of said housing.

15. The ultrasonic transducer as claimed in claim 1 wherein the thickness of the tape is from 1.0 to 20.0 mil thick.

16. The ultrasonic transducer as claimed in claim 1 wherein said tape is of polyethylene material.

17. An ultrasonic transducer comprising:
   an ultrasonic transducer for detecting liquid in a vessel or tube; said transducer comprising
      a housing,
      a piezoelectric element within said housing facing one end of said housing, and
      signal leads connected to said piezoelectric element that extend out from said housing;
   an electronic circuit to which said signal leads are connected to at least one of supply electrical energy to be transmitted by said transducer piezoelectric element as ultrasonic energy and/or receive electrical signals corresponding to ultrasonic energy received by said transducer piezoelectric element; and
   a piece of double sided adhesive tape having one adhesive side secured directly to the outer face of said one end of said housing with the other adhesive side to be secured directly to the outer surface of the wall of a pipe or vessel and being of a material and thickness to effectively couple the ultrasonic energy in at least one of transmitting and receiving directions between said piezoelectric element, the pipe or vessel wall on which the transducer is mounted and a liquid in the pipe or vessel.

* * * * *